United States Patent [19]

Bilweis

[11] 4,084,692
[45] Apr. 18, 1978

[54] DISPENSER FOR SURGICAL THREADS

[75] Inventor: Joseph Bilweis, Noisy-le-Roi, France

[73] Assignee: Ethicon, Inc., Somerville, N.J.

[21] Appl. No.: 659,075

[22] Filed: Feb. 18, 1976

Related U.S. Application Data

[63] Continuation-in-part of Ser. No. 605,791, Aug. 18, 1975, abandoned.

[30] Foreign Application Priority Data

Sep. 3, 1974 France .................................. 74 29955

[51] Int. Cl.² .............................................. A61L 17/02
[52] U.S. Cl. ..................................... 206/403; 206/63.3;
206/815; 224/28 F; 242/137.1
[58] Field of Search ....................... 242/137, 137.1, 138,
242/139, 170, 171, 126, 129, 132, 174–178;
206/63.3, 225, 227, 496, 815, 406, 403, 310, 405,
63.5; 128/340, 334 R; 63/15.45; 132/92 R, 92
A; 224/28 F, 403

[56] References Cited

U.S. PATENT DOCUMENTS

| 1,260,011 | 3/1918 | Muchow | 132/92 R |
|---|---|---|---|
| 1,627,525 | 5/1927 | Munro | 132/92 R |
| 2,365,647 | 12/1944 | Ogburn | 128/340 |
| 2,522,379 | 9/1950 | Kissner | 206/496 |
| 2,785,797 | 3/1957 | Rice | 206/310 |
| 2,796,067 | 6/1957 | McCutcheon | 206/496 |
| 2,882,388 | 4/1959 | Garland | 220/94 A |
| 2,893,548 | 7/1959 | Carver, Jr. et al. | 206/63.3 |
| 2,938,624 | 5/1960 | Runkel et al. | 206/63.6 |
| 3,154,193 | 10/1964 | Alden | 206/405 |
| 3,263,444 | 8/1966 | Di Croce | 63/15.45 |
| 3,361,382 | 1/1968 | Converse | 242/137.1 |
| 3,370,698 | 2/1968 | Geier | 206/405 |
| 3,424,435 | 1/1969 | Niemann | 206/405 |
| 3,648,949 | 3/1972 | Berger et al. | 206/227 |
| 3,749,238 | 7/1973 | Taylor | 206/227 |
| 3,907,109 | 9/1975 | Primicerio et al. | 206/406 |
| 3,993,230 | 11/1976 | Oakes | 206/815 |

FOREIGN PATENT DOCUMENTS 624,072 8/1961 Italy .................................. 206/63.6

Primary Examiner—William T. Dixon, Jr.
Assistant Examiner—Allan N. Shoap
Attorney, Agent, or Firm—Wayne R. Eberhardt

[57] ABSTRACT

A surgical thread dispenser comprising a reel for holding the thread wound thereon, a reel case enclosing the reel on one side and around the periphery thereof with an opening in the periphery for dispensing the thread, and a finger ring attached to the casing and adapted so that when the ring is placed over one finger of the surgical practitioner, the reel case is positioned in the palm of the practitioner's hand and lengths of the surgical thread may be conveniently withdrawn from the dispenser.

8 Claims, 11 Drawing Figures

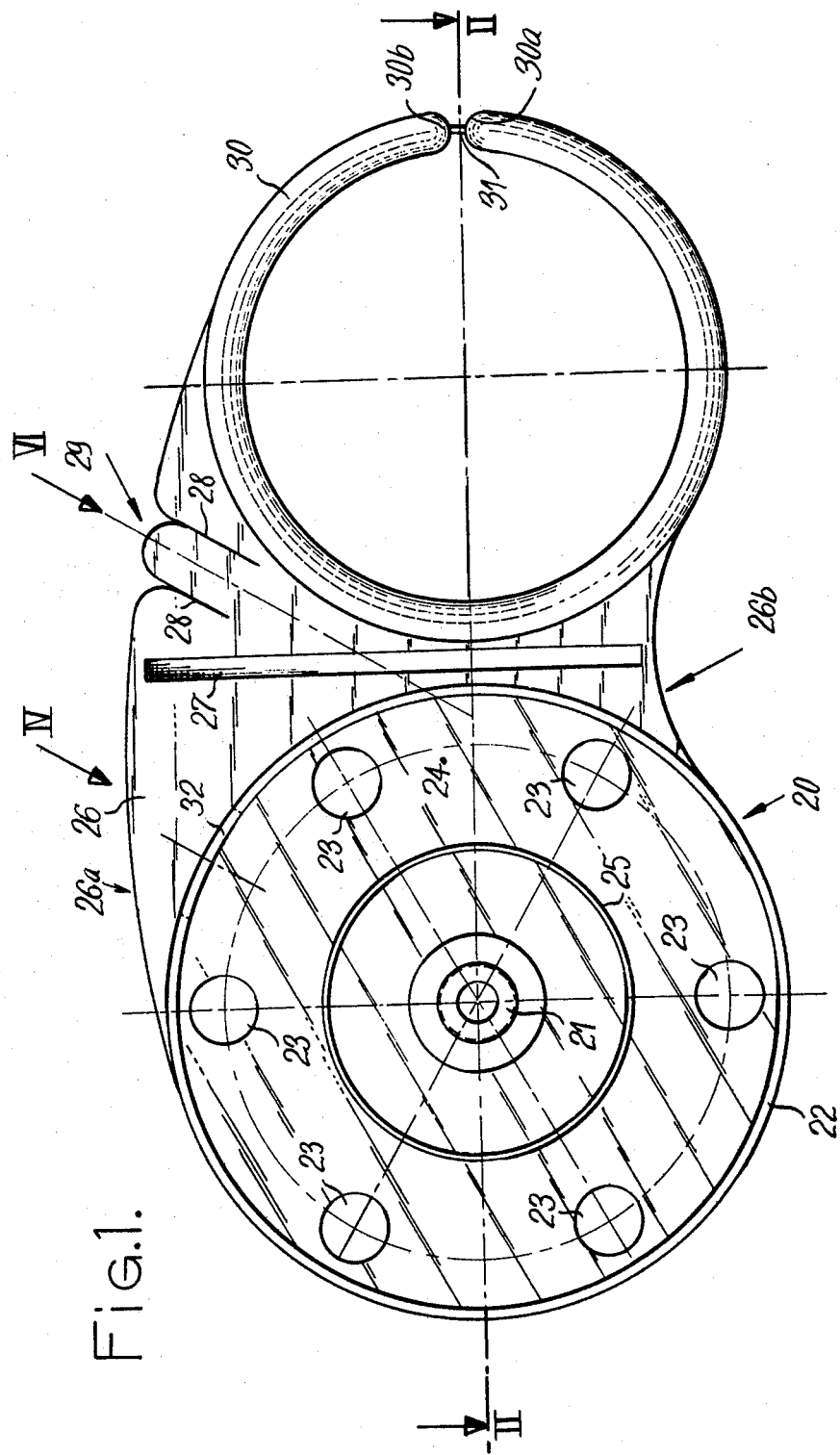

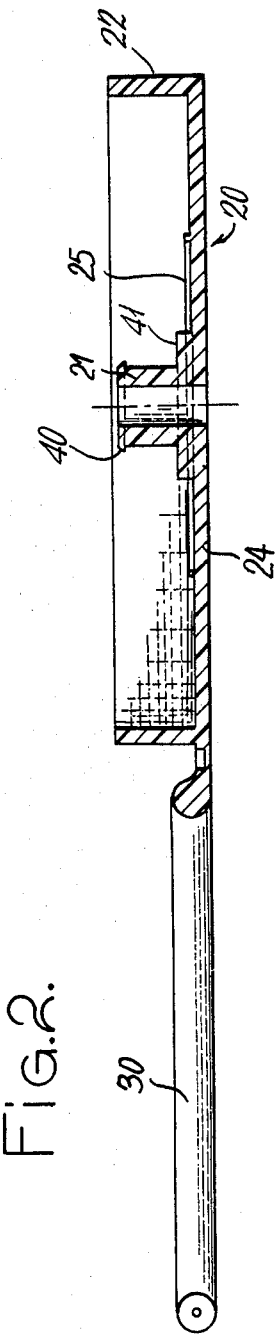
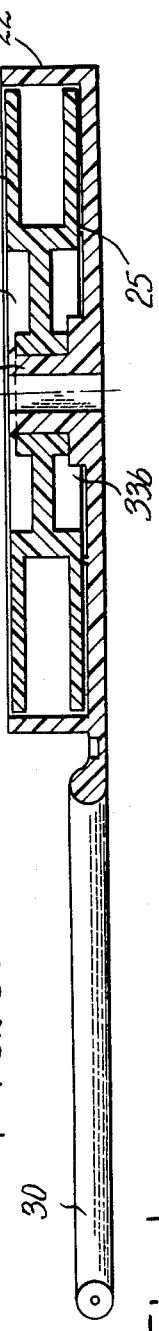
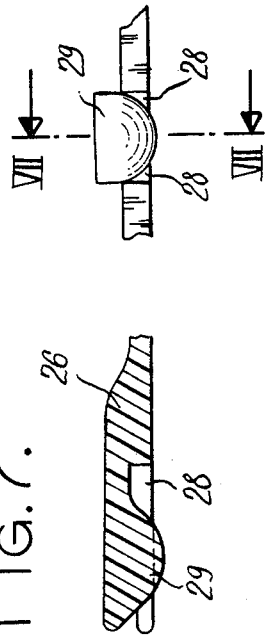
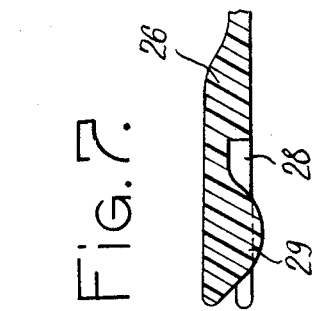
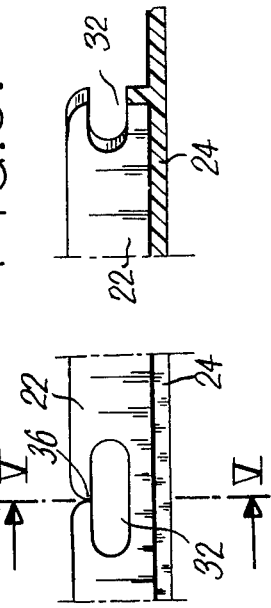

DISPENSER FOR SURGICAL THREADS

RELATIONSHIP WITH CO-PENDING APPLICATIONS

This is a continuation-in-part of Ser. No. 605,791 filed Aug. 18, 1975, now abandoned.

BACKGROUND OF THE INVENTION

1. Field of the Invention

This invention relates to dispensers for surgical threads, and more particularly to a reel and case for storing, holding and dispensing surgical threads.

2. Background of the Invention

During a surgical intervention, there is a need for the surgeon to use thread for ligaturing and suturing. The surgical thread is very frequently packaged as a coil in a protective tube and unwinding it causes a tendency to kink. This kinking is unpleasant, annoys the surgeon, and increases the duration of the intervention. In certain cases, there is a risk of the thread knotting or being damaged as a result of this kinking.

Many designs have been proposed for holding and dispensing surgical threads, including a variety of spool and reel type devices, as illustrated for example in U.S. Pat. Nos. 2,893,548; 2,938,624;, 3,095,159; and 3,376,973. While several of these devices effectively prevent the suture from kinking or tangling as it is being removed from the dispenser, the dispensers tend to be easily dropped or misplaced during use. Some dispensers which are adapted to be slipped over the finger of the practitioner during use tend to interfere with the ligaturing or suturing operation, or are otherwise inconvenient to use.

The present invention remedies these disadvantages by providing a reel and case for surgical thread which is easily and conveniently manipulated by the surgeon and permits the surgical thread to be removed in any length desired by the practitioner, with the other portion remaining in the case for preservation. The case is equipped with a finger element that permits the surgeon to hold it in the palm of his right or left hand according to his needs without reducing the ability to manipulate his fingers.

SUMMARY

The surgical thread dispenser of the present invention comprises a flat, cylindrical reel for holding a surgical thread wound thereon, a case for said reel enclosing the reel on one side and around the outer periphery thereof with an opening in the peripheral rim of the case through which the thread is dispensed from the reel, and a split finger ring affixed to the reel case through an arcuate membrane which enables the practitioner to hold the reel case in the palm of his hand while his fingers remain unencumbered.

BRIEF DESCRIPTIONS OF DRAWINGS

FIG. 1 is a plan view of the dispenser casing;

FIG. 2 is a lateral elevation view cross section in part, taken only line II—II of FIG. 1;

FIG. 3 is an elevation view, cross sectional in part, similar to FIG. 2, but showing the reel in cross section in the casing;

FIG. 4 is a partial view taken along arrow IV of FIG. 1;

FIG. 5 is a cross-sectional view taken along line V—V of FIG. 4;

FIG. 6 is a partial elevation view taken along arrow VI of FIG. 1;

FIG. 7 is a cross-sectional view taken along line VII—VII of FIG. 6.

DESCRIPTION OF PREFERRED EMBODIMENTS

Figure 10:
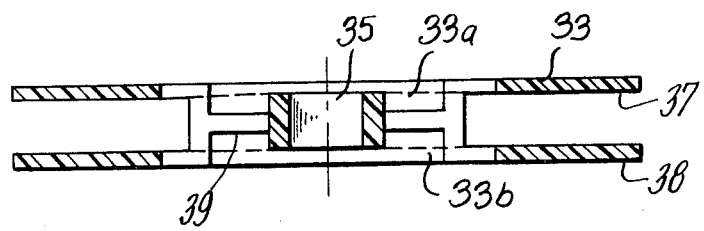
FIG. 10 is a cross-sectional view taken along line X—X of FIG. 8.
Figure 9:
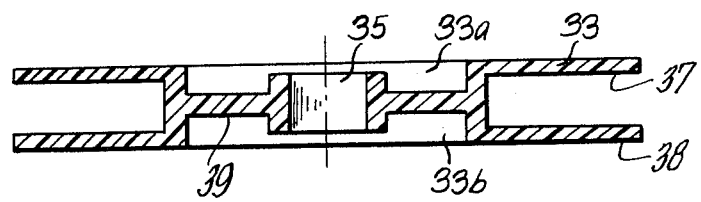
FIG. 9 is a cross-sectional view taken along line IX—IX of FIG. 8.
Figure 8:
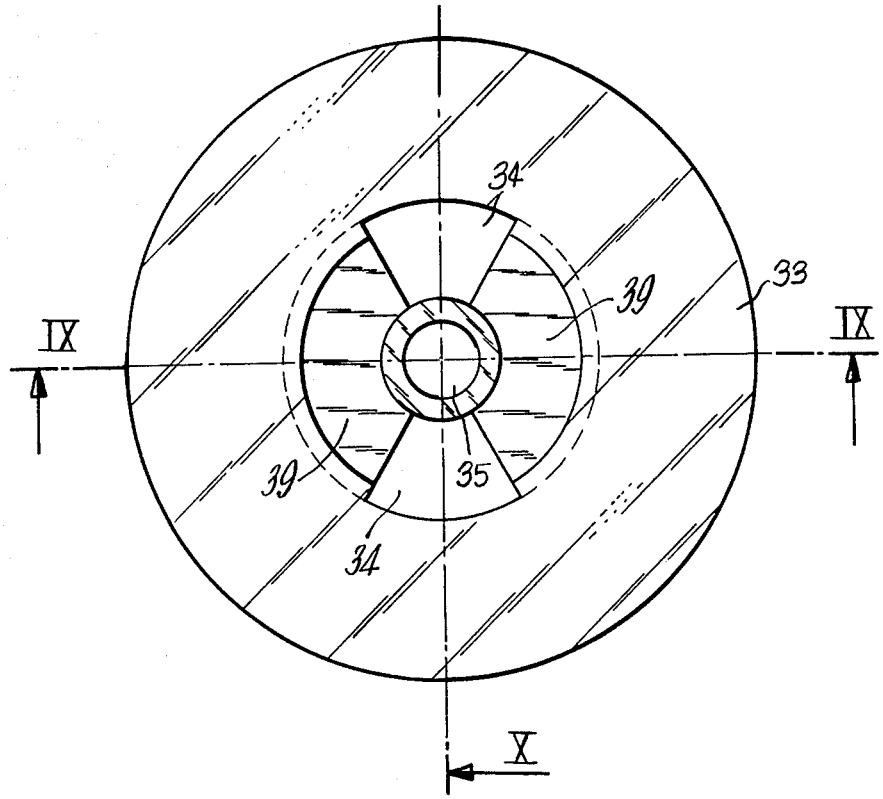
FIG. 8 is a plan view of the reel.

In accordance with the present invention, the casing for the reel for surgical threads, such as suture or ligature threads for the surgeon or other practitioner, is characterized in that the casing is composed of a receptacle, generally of a cylindrical shape, comprising a circular backing plate and a rim extending from the periphery thereof, and, in the center of the backing plate, a spindle provided to receive a reel containing the surgical thread, this thread being dispensed from the reel through an opening in the outer rim of the case. The backing plate of the case is extended by a membrane or arcuate tail holding a split ring adapted to be placed on one of the practitioner's fingers.

According to one feature of the invention, the suture dispenser is characterized in that the membrane or arcuate tail is provided with a line of weakness which allows the finger ring to be bent to an angle with the plane of the suture reel and enables the practitioner to easily hold the dispenser in the palm of his hand while retaining complete freedom of his fingers.

With specific reference to FIGS. 1 and 2, the suture casing comprises cylindrically shaped receptacle 20 comprising backing plate 24 and in its center, spindle 21 having substantially the same height as peripheral edge or rim 22. Plate 24 of the receptacle optionally contains a plurality of openings 23 and a circumferential reel support ridge 25 spaced intermediate spindle 21 and rim 22. Plate 24 of the receptacle is extended by arculate membrane 26 having outwardly rounded edge 26a and opposite inwardly rounded or hollowed edge 26b.

Membrane 26 terminates in finger ring 30 of which opposing members 30a and 30b are preferably joined by low strength member 31. Outwardly rounded edge 26a of membrane 26 optionally includes suture retaining element 29 comprising a pair of parallel cuts 28 located intermediate receptacle 20 and finger ring 30.

Membrane 26 is further optionally provided with groove 27 extending transversely across the membrane intermediate receptical 20 and finger ring 30. Groove 27 constitutes a line of weakness along which the membrane may be flexed to provide an angle between the plane of the finger ring and the plane of the receptacle to facilitate holding the suture casing in the palm of the hand of the practitioner.

Peripheral rim 22 of receptacle 20 includes opening 32 through which the surgical thread can pass from the reel to the outside of the casing. Detail of one suitable opening is illustrated in FIG. 4 where elongated opening 32 is centrally located in rim 22 and is provided with slot 36 to allow the suture to be slipped into the opening. Further detail of opening 32 is illustrated in cross section in FIG. 5.

With reference to FIG. 3 and FIGS. 8-10, there is illustrated suture reel 33 comprising two spaced and parallel flange portions joined by central hub 39 which contains axial opening 35. The embodiment of reel 33 illustrated in FIG. 8 includes two openings 34 in web 39 which adapt the reel to fit the pins of a winding machine to facilitate winding the surgical thread upon the reel. Axial opening 35 is sized to fit over spindle 21 of the receptacle to allow reel 33 to turn freely thereon.

With reference to FIGS. 2 and 3, spindle 21 is preferably provided with reel restraining lip 40 to prevent the reel from slipping off spindle 21 once it has been snapped into place. Spindle 21 is also preferably equipped with shoulder 41 at the base thereof to provide a bearing surface for reel hub 39. The distance between shoulder 41 and lip 40 of spindle 21 corresponds to the thickness of hub 39 at axial opening 35. Ridge 25 serves to support reel 33 to facilitate the turning thereof as suture is withdrawn from the reel. Reel 33 is preferably symmetrical in design so that it may be placed into receptacle 20 without regard for a top or bottom.

With reference to FIGS. 6 and 7, there is illustrated a preferred configuration for optional surgical thread holding element 29 which allows the thread to be quickly and surely put into and removed from a fixed position under the holding element during use.

Figure 11:
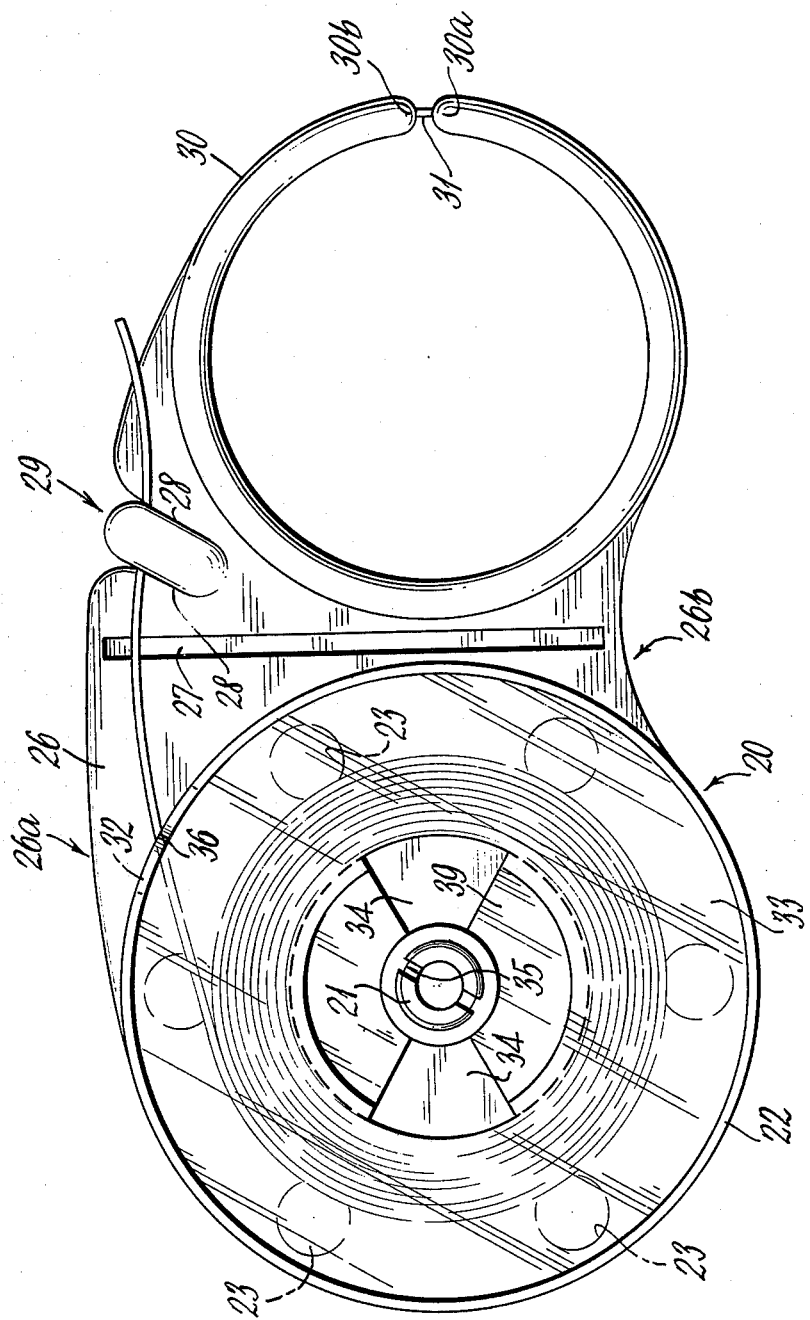
FIG. 11 is a plan view of the dispenser with reel and surgical thread.

With final reference to FIG. 11, there is illustrated a suture case of the present invention with a length of suture extending therefrom and restrained in the suture holding means in accordance with a preferred use of the invention.

When the practitioner desires to use the reel casing of the present invention, he introduces one finger of his right or left hand into ring 30 and can thus have at his disposal, by pulling slightly on the thread from the reel, the desired length of thread while he is performing an operation.

The dispenser for surgical thread, as above described, is adapted to receive any diameter of ligature and suture threads, of braided or monofilament construction, and of any predetermined length. The construction of the dispenser prevents the unit, thread and casing, from rolling on the operative field when the dressing nurse is working with the surgeon, or even during the utilization of the unit by the surgeon should he temporarily remove it from his finger. It allows the surgeon to hold the unit in the hollow of his right or left hand while providing him free use of his 10 fingers. During the utilization of the thread, the portion of the thread remaining on the reel is afforded maximum protection against suture damage, and the surgeon can check the remaining length of thread since the reel is preferably made of translucent material. There are thus prevented many interferences usually associated with spooled sutures and which are prejudicial to the efficiency of a surgical process.

The surgical thread is not damaged when being removed from the supporting reel or by the thread holding element. The thread starts perfectly free on the reel and, at the end of the winding, it is still free and ready for use.

When the surgeon has finished the operation, he has the ability to free his finger of the dispenser by simply pulling on the casing, which causes the ring to separate by breaking the low strength connecting portion 31, quickly freeing the surgeon's finger.

The holes 23 in the bottom of the casing provide a fast and efficient flow of ethylene oxide or other sterilization fluid when the dispenser unit is sterilized. Such holes may be omitted where the unit is to be sterilized by heat or radiation.

The invention is not restricted to the embodiment shown and described in detail, and various modifications thereof will be apparent to those skilled in the art and be applied thereto without departing from the scope of the present invention.

What is claimed is:

1. A surgical thread dispenser comprising:
    a. a flat, cylindrical reel comprising a hub having an axial opening therein and flanges on each side of said hub which in cooperation with each other and said hub form an annular groove adapted to carry a length of surgical thread wound thereon in a plurality of turns;
    b. a reel case comprising a circular backing plate at one side of the reel having a centrally located spindle extending outward from said backing plate for supporting the hub of said reel, the outside diameter of said spindle being sized to receive the axial opening in said hub to allow the reel to rotate freely on said spindle, the backing plate having an annular peripheral rim extending radially beyond the outer periphery of said reel and axial beyond the outer flange of said reel, said rim having an opening therein for dispensing the surgical thread from the reel through the rim;
    c. a finger ring sized to accept the middle finger of an adult human hand, and oriented in the same plane as said backing plate; and
    d. a membrane extending between said finger ring and said backing plate and having a line of weakness extending transversely across the width of the membrane intermediate said finger ring and said backing plate,
said finger ring being spaced from said backing plate a distance that when the finger ring is placed over a middle finger of a hand and the membrane is bent along said line of weakness to provide an angle between the plane of the finger ring and the plane of the backing plate, the dispenser is positioned in the palm of the hand and the suture is available for withdrawing from the reel through the opening in the rim of the case.

2. A surgical thread dispenser of claim 1 wherein the finger ring is split.

3. A surgical thread dispenser of claim 2 wherein the ends of the split finger ring are connected by a member of low strength.

4. A surgical thread dispenser of claim 1 wherein the membrane is provided with suture holding means.

5. A surgical thread dispenser of claim 1 wherein the membrane is arcuate.

6. A surgical thread dispenser of claim 1 wherein the spindle of the reel case includes a reel restraining lip at the end opposite the backing plate.

7. A surgical thread dispenser of claim 1 wherein the spindle of the reel case has a reel bearing surface at the base of the spindle to space the reel flange from the surface of the backing plate.

8. A surgical thread dispenser of claim 1 wherein the backing plate has a circumferential reel support ridge positioned intermediate the spindle and peripheral rim of the backing plate.

* * * * *